US009469582B2

(12) United States Patent
Mills et al.

(10) Patent No.: US 9,469,582 B2
(45) Date of Patent: Oct. 18, 2016

(54) POLYOLEFIN MANUFACTURING SYSTEM INCLUDING A MEMBRANE FRACTIONATION SYSTEM FOR DILUENT RECOVERY

(71) Applicant: Chevron Phillips Chemical Company LP, The Woodlands, TX (US)

(72) Inventors: Andrew J. Mills, Houston, TX (US); Andrea L. Hoener, Kingwood, TX (US); Ralph W. Romig, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 14/968,828

(22) Filed: Dec. 14, 2015

(65) Prior Publication Data

US 2016/0096783 A1    Apr. 7, 2016

Related U.S. Application Data

(62) Division of application No. 12/829,228, filed on Jul. 1, 2010, now Pat. No. 9,211,523.

(51) Int. Cl.

| C07C 7/04 | (2006.01) |
|---|---|
| C07C 7/144 | (2006.01) |
| C08F 2/14 | (2006.01) |
| C08F 6/00 | (2006.01) |
| B01D 3/14 | (2006.01) |
| B01D 61/58 | (2006.01) |
| B01D 63/00 | (2006.01) |
| C07C 7/00 | (2006.01) |
| C08F 6/06 | (2006.01) |
| C08F 6/04 | (2006.01) |
| B01J 19/18 | (2006.01) |

(52) U.S. Cl.
CPC .............. *C07C 7/005* (2013.01); *B01D 3/14* (2013.01); *B01D 61/58* (2013.01); *B01D 63/00* (2013.01); *B01J 19/1837* (2013.01); *C07C 7/04* (2013.01); *C07C 7/144* (2013.01); *C08F 2/14* (2013.01); *C08F 6/001* (2013.01); *C08F 6/04* (2013.01); *C08F 6/06* (2013.01); *B01D 2311/02* (2013.01); *B01D 2311/2669* (2013.01); *B01D 2311/2696* (2013.01); *B01D 2317/02* (2013.01); *B01D 2317/022* (2013.01); *B01D 2317/025* (2013.01)

(58) Field of Classification Search
CPC .......... C07C 7/144; C08F 6/001; C08F 6/06; B01D 3/14; B01D 63/00
USPC .......................................... 528/482; 585/818
See application file for complete search history.

(56) References Cited

U.S. PATENT DOCUMENTS

| 4,374,657 A | 2/1983 | Schendel et al. |
|---|---|---|
| 5,085,776 A | 2/1992 | Blume et al. |
| 5,281,255 A | 1/1994 | Toy et al. |
| 6,114,501 A | 9/2000 | Hottovy et al. |
| 6,262,191 B1 | 7/2001 | Hottovy et al. |

(Continued)

*Primary Examiner* — Fred M Teskin
(74) *Attorney, Agent, or Firm* — Fletcher Yoder, P.C.

(57) ABSTRACT

A fractionation system for a polymerization reactor includes a membrane separation system designed to separate light components, such as unreacted monomer and inerts, from diluent. The membrane separation system may employ one or more membrane modules designed to separate hydrocarbons based on size, solubility, or combinations thereof. The fractionation system also may include a heavies fractionation column designed to separate heavy components, such as unreacted comonomer and oligomers, from the diluent.

20 Claims, 4 Drawing Sheets

(56) References Cited

U.S. PATENT DOCUMENTS

| | | |
|---|---|---|
| 6,559,247 B2 | 5/2003 | Kufeld et al. |
| 6,559,348 B1 | 5/2003 | Aittamaa et al. |
| 6,818,186 B2 | 11/2004 | Burns et al. |
| 6,838,531 B2 | 1/2005 | Reid et al. |
| 7,070,694 B2 | 7/2006 | Colling et al. |
| 7,087,685 B2 | 8/2006 | Burns et al. |
| 7,351,779 B2 | 4/2008 | Iaccino et al. |
| 7,524,904 B2 | 4/2009 | Verser et al. |
| 2006/0063896 A1 | 3/2006 | McElvain et al. |
| 2007/0142576 A1 | 6/2007 | Tait et al. |

POLYOLEFIN MANUFACTURING SYSTEM INCLUDING A MEMBRANE FRACTIONATION SYSTEM FOR DILUENT RECOVERY

This application is a division of U.S. application Ser. No. 12/829,228 filed Jul. 1, 2010, now U.S. Pat. No. 9,211,523, which is hereby incorporated by reference in its entirety for all purposes.

BACKGROUND

The present disclosure relates generally to polyolefin production, and more particularly, to membrane fractionation systems employed in polyolefin production to facilitate diluent recovery.

This section is intended to introduce the reader to aspects of art that may be related to aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

As chemical and petrochemical technologies have advanced, the products of these technologies have become increasingly prevalent in society. In particular, as techniques for bonding simple molecular building blocks into longer chains (or polymers) have advanced, the polymer products, typically in the form of various plastics, have been increasingly incorporated into various everyday items. For example, polyolefin polymers, such as polyethylene, polypropylene, and their copolymers, are used for retail and pharmaceutical packaging, food and beverage packaging (such as juice and soda bottles), household containers (such as pails and boxes), household items (such as appliances, furniture, carpeting, and toys), automobile components, pipes, conduits, and various industrial products.

Specific types of polyolefins, such as high-density polyethylene (HDPE), have particular applications in the manufacture of blow-molded and injection-molded goods, such as food and beverage containers, film, and plastic pipe. Other types of polyolefins, such as low-density polyethylene (LDPE), linear low-density polyethylene (LLDPE), isotactic polypropylene (iPP), and syndiotactic polypropylene (sPP) are also suited for similar applications. The mechanical requirements of the application, such as tensile strength and density, and/or the chemical requirements, such thermal stability, molecular weight, and chemical reactivity, typically determine what polyolefin or type of polyolefin is suitable.

One benefit of polyolefin construction, as may be deduced from the list of uses above, is that it is generally non-reactive with goods or products with which it is in contact. This allows polyolefin products to be used in residential, commercial, and industrial contexts, including food and beverage storage and transportation, consumer electronics, agriculture, shipping, and vehicular construction. The wide variety of residential, commercial, and industrial uses for polyolefins has translated into a substantial demand for raw polyolefin, which can be extruded, injected, blown, or otherwise formed into a final consumable product or component.

To satisfy this demand, various processes exist by which olefins may be polymerized to form polyolefins. Typically, these processes are performed at or near petrochemical facilities, which have ready access to the short-chain olefin molecules (monomers and comonomers) such as ethylene, propylene, butene, pentene, hexene, octene, decene, and other building blocks of the much longer polyolefin polymers. These monomers and comonomers may be polymerized in a liquid-phase polymerization reactor and/or gas-phase polymerization reactor to form polymer (polyolefin) solid particulates, typically called fluff or granules. The fluff may possess one or more melt, physical, rheological, and/or mechanical properties of interest, such as density, melt index (MI), melt flow rate (MFR), copolymer content, comonomer content, modulus, and crystallinity. The reaction conditions within the reactor, such as temperature, pressure, chemical concentrations, polymer production rate, and so forth, may be selected to achieve the desired fluff properties.

In addition to the one or more olefin monomers and/or comonomers, a catalyst for facilitating the polymerization may be added to the reactor. For example, the catalyst may include particles added to the reactor in a reactor feed stream to produce catalyst particles suspended in the fluid medium within the reactor. An example of such a catalyst is a chromium oxide containing hexavalent chromium on a silica support. Further, a diluent may be introduced into the reactor. The diluent may be an inert hydrocarbon, such as isobutane, propane, n-pentane, i-pentane, neopentane, and n-hexane that is liquid at reaction conditions. Further, some polymerization processes may not employ a separate diluent, such as in the case of selected examples of polypropylene production where the propylene monomer itself acts as the diluent.

The effluent discharged from the reactor typically includes the polymer fluff as well as non-polymer components, such as unreacted olefin monomer (and comonomer), diluent, inerts, other hydrocarbons, and so forth. In the case of polyethylene production in liquid phase reactors, such as loop slurry reactors, the non-polymer components primarily include diluent, such as isobutane, having a small amount of unreacted ethylene (e.g., 5 wt. %) and other entrained hydrocarbons. For polypropylene production, the non-polymer components primarily include unreacted propylene monomer having a small amount of other entrained hydrocarbons. The reactor effluent is generally processed, such as by an effluent treatment system, to separate the non-polymer components from the polymer fluff. The polymer fluff may then be treated to deactivate residual catalyst, remove entrained hydrocarbons, dry the polymer, and pelletize the polymer in an extruder, and so forth, before the polymer is sent to a customer.

The non-polymer components, such as the recovered diluent, unreacted monomer, and other non-polymer components from the effluent treatment system, may be treated within a fractionation system to separate most of the recovered diluent from the other non-polymer components. The recovered diluent may ultimately be returned as purified or treated feed to the reactor while the other non-polymer components may be flared or returned to the supplier, such as to an olefin manufacturing plant or petroleum refinery. Typically, the fractionation system may employ fractionation columns to separate the diluent from the other non-polymer components. One or more of the fractionation columns may employ cold temperatures to facilitate separation of some of the components, particularly those with lower boiling points than the diluent. To achieve the cold temperatures, refrigeration systems may be employed within the fractionation columns. However, it is now recognized that the refrigeration systems may be costly to operate, install, and/or maintain.

BRIEF DESCRIPTION OF THE DRAWINGS

Advantages of the present disclosure may become apparent upon reading the following detailed description and upon reference to the drawings in which.

DETAILED DESCRIPTION OF SPECIFIC EMBODIMENTS

Figure 1:
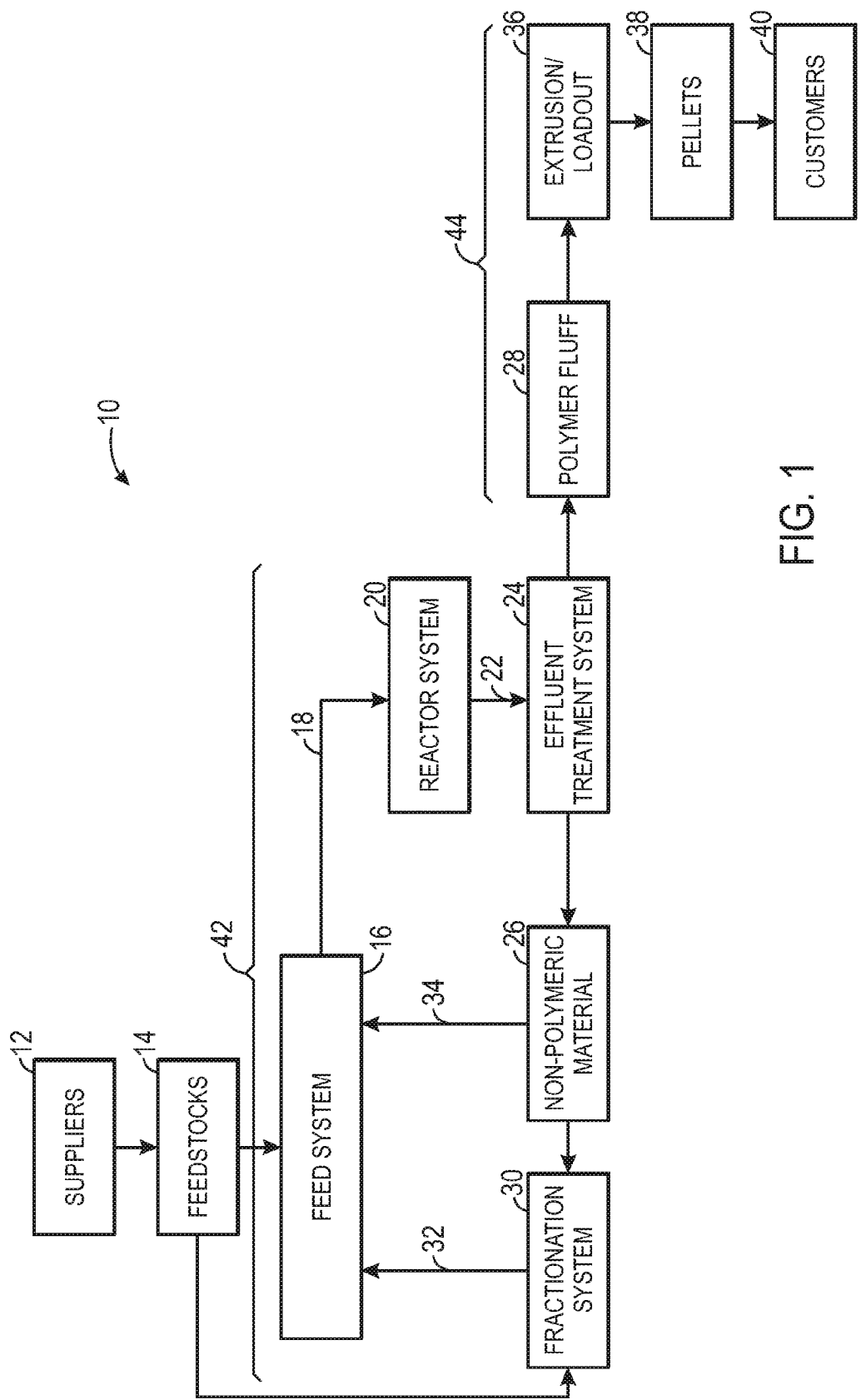
FIG. 1 is a block flow diagram of a polyolefin manufacturing system for the production of polyolefins, which includes a membrane separation system within a fractionation system in accordance with present embodiments.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure is directed to polyolefin manufacturing systems that incorporate fractionation systems with membranes that separate non-polymer components from the diluent. In general, fractionation systems may be employed to separate light components or "lights" and heavy components or "heavies" from the diluent. As used herein, light components or "lights" may refer to components with lower boiling points than the diluent employed, and heavy components or "heavies" may refer to those components with higher boiling points than the diluent employed. For example, in polyethylene production where isobutane is the diluent, lights may include unreacted monomer (e.g., ethylene), other hydrocarbons (e.g., ethane), and other components (e.g., hydrogen and nitrogen), among others, while heavies may include unreacted comonomer (e.g., 1-butene), oligomers, and other hydrocarbons (e.g., hexane), among others.

In general, fractionation columns may be employed to separate the non-polymer components from the diluent. For example, the fractionation systems disclosed herein may employ one or more fractionation columns to separate the heavy components from the diluent. However, to separate the light components from the diluent, the fractionation systems disclosed herein may employ one or more hydrocarbon absorption membranes instead of fractionation columns. Indeed, it is now recognized that the use of such membranes for lights separation may reduce operating, capital, and/or maintenance costs when compared to the costs incurred when using traditional fractionation columns for lights separation.

In general, fractionation columns may separate components based on differences in boiling points. However, light components may have very low boiling points. Accordingly, a lights fractionation column typically employs a refrigeration system to achieve temperatures low enough to facilitate separation of the light components. The refrigeration system may include rotating equipment and associated piping, which may increase maintenance, capital, and/or operating costs relative to a process that does not include a refrigeration system. Further, additional expenses may be incurred with higher throughputs because the operating efficiency of the refrigeration system may be affected by load variations in the fractionation system. Moreover, inclusion of extra equipment may be required by aspects related to operation of the refrigeration system, which may increase costs and/or complexity. For example, a dryer may be included upstream of a lights fractionation column to remove water, which may freeze at the low temperatures produced by the refrigeration system.

In contrast to the traditional use of fractionation columns for lights separation, the hydrocarbon absorption membranes may separate the light components based on solubility, size, or both, without using a refrigeration system. Accordingly, it is now recognized that capital, maintenance, and/or operating costs may be reduced relative to traditional separation system by eliminating the need for a refrigeration system. Further, the operating efficiency of the hydrocarbon absorption membranes may not be affected by load variations. Moreover, the fractionation systems employing hydrocarbon absorption membranes may provide increased diluent recovery relative to fractionation systems not employing hydrocarbon absorption membranes. For example, according to certain embodiments, it is believed that the fractionation systems disclosed herein may provide diluent recovery of at least approximately 99.99 percent of the diluent in the reactor effluent. The fractionation systems disclosed herein may be particularly well suited to polyolefin manufacturing processes employing loop slurry reactors. However, the fractionation system disclosed herein also may be employed in polyolefin manufacturing processes that utilize other types of liquid phase reactors as well.

FIG. 1 depicts an exemplary manufacturing system 10 for producing polyolefins, such as polyethylene homopolymer, copolymer, and/or terpolymer, among others. Various suppliers 12 may provide reactor feedstocks 14 to the manufacturing system 10 via pipelines, trucks, cylinders, drums, and so forth. The suppliers 12 may include off-site and/or on-site facilities, such as olefin plants, refineries, catalyst plants, and the like. Examples of possible feedstocks 14 include olefin monomers and comonomers (e.g., ethylene, propylene, butene, hexene, octene, and decene), diluents (e.g., propane, isobutane, n-hexane, and n-heptane), chain transfer agents (e.g., hydrogen), catalysts (e.g., Ziegler catalysts, Ziegler-Natta catalysts, chromium catalysts, and metallocene catalysts), co-catalysts (e.g., triethylaluminum alkyl, triethylboron, and methyl aluminoxane), and other additives.

According to certain embodiments, ethylene feedstock may be supplied by one or more pipelines at approximately 55-100 bar (800-1450 pounds per square inch gauge (psig)) at approximately 7-18° C. (45-65° F.). In another example, hydrogen feedstock may be supplied by pipeline at approximately 62-69 bar (900-1000 psig) at approximately 32-43° C. (90-110° F.). As may be appreciated, the types, combinations, and/or supply methods of the feedstocks may vary depending on factors, such as production capacity, location, design criteria, and the desired type of polyolefin product, among others.

The suppliers 12 may provide the feedstocks 14 to a reactor feed system 16 where the feedstocks 14 may be stored, such as in monomer storage and feed tanks, diluent vessels, catalyst tanks, co-catalyst cylinders and tanks, and so forth. Within the feed system 16, the feedstocks 14 may be treated and/or processed to produce feed streams 18 for a reactor system 20. For example, the feed system 16 may include treatment beds (e.g., molecular sieve beds, aluminum packing, etc.) that remove catalyst poisons from the feedstocks 14. According to certain embodiments, the catalyst poisons may include water, oxygen, carbon monoxide, carbon dioxide, and organic compounds containing sulfur, oxygen, or halogens, among others.

The feed system 16 also may prepare or condition the feedstocks 14 for addition to polymerization reactors in the reactor system 20. For example, a catalyst may be activated and then mixed with diluent (e.g., isobutane or hexane) or mineral oil in catalyst preparation tanks. Further, the feed system 16 may meter and control the addition rate of the feedstocks 14 into the reactor system 20 to maintain the desired reactor stability and/or to achieve the desired polyolefin properties or production rate.

In addition to processing the feedstocks 14, the feed system 16 may store, treat, and meter recovered reactor effluent for recycle to the reactor system 20. For example, diluent may be recovered from the reactor effluent and recycled to the reactor system 20. According to certain embodiments, only a relatively small amount of fresh make-up diluent may be utilized in the feedstocks 14, while a majority of the diluent fed to the reactor system 20 may be recovered from the reactor effluent. In another example, catalyst may be recovered from the reactor effluent and recycled to the reactor system 20.

In summary, the feedstocks 14 and the recovered reactor effluent are processed in the feed system 16 and fed as feed streams 18 (e.g., streams of monomer, comonomer, diluent, catalysts, co-catalysts, hydrogen, additives, or combinations thereof) to the reactor system 20. The feed streams 18 may be liquid, gaseous, or a supercritical fluid, depending on the type of reactor or reactors within the reactor system 20.

The reactor system 20 may include one or more polymerization reactors, such as liquid-phase reactors, gas-phase reactors, or a combination thereof. Multiple reactors may be arranged in series, in parallel, or in any other suitable combination or configuration. Within the polymerization reactors, one or more olefin monomers and/or comonomers may be polymerized to form a product containing polymer particulates, typically called fluff or granules. According to certain embodiments, the olefin monomers and comonomers may include 1-olefins having up to 10 carbon atoms per molecule and typically no branching nearer the double bond than the 4-position. For example, the monomers and comonomers may include ethylene, propylene, butene, 1-pentene, 1-hexene, 1-octene, and 1-decene. The fluff may possess one or more melt, physical, rheological, and/or mechanical properties of interest, such as density, melt index (MI), melt flow rate (MFR), copolymer or comonomer content, modulus, and crystallinity. The reaction conditions, such as temperature, pressure, flow rate, mechanical agitation, product takeoff, component concentrations, polymer production rate, and so forth, may be selected to achieve the desired fluff properties.

The catalyst within the feed stream 18 may facilitate polymerization of the monomer within the reactor vessels. According to certain embodiments, the catalyst may include particles suspended in the fluid medium within the reactor. In general, Ziegler catalysts, Ziegler-Natta catalysts, metallocenes, and other well-known polyolefin catalysts, as well as co-catalysts, may be used. According to certain embodiments, the catalyst may be a chromium oxide catalyst containing hexavalent chromium on a silica support.

The diluent within the feed stream 18 may be used to suspend the catalyst particles and the formed polymer particles within the reactor vessels. According to certain embodiments, the diluent may be an inert hydrocarbon that is liquid at reaction conditions, such as isobutane, propane, n-butane, n-pentane, i-pentane, neopentane, n-hexane, cyclohexane, cyclopentane, methylcyclopentane, or ethylcyclohexane, among others.

One or more motive devices may be present within the reactor vessels in the reactor system 20. For example, within a liquid-phase reactor, such as a loop slurry reactor, an impeller may create a turbulent mixing zone within the fluid medium. The impeller may be driven by a motor to propel the fluid medium as well as any catalyst, polymer particles, or other solid particulates suspended within the fluid medium, through the closed loop of the reactor.

The formed polymer particles, as well as non-polymer components, such as the diluent, unreacted monomer/comonomer, and residual catalyst, may exit the reactor system 20 as effluent 22. After leaving the reactor system 20, the effluent 22 may be subsequently processed, such as by an effluent treatment system 24, to separate the non-polymer components 26 (e.g., diluent, unreacted monomer, and comonomer) from the formed polymer particles. After separation, the formed polymer particles may exit the effluent treatment system 24 as polymer fluff 28.

The non-polymer components 26 may be processed, for example, by a fractionation system 30, to remove undesirable light and heavy components and produce fractionated product streams 32. The fractionated product streams 32 may then be returned to the reactor system 20 via the feed system 16. In addition, some or all of the non-polymer components 26 may bypass the fractionation system 30 to be recycled more directly to the feed system 16 as non-fractionated product streams 34. Additionally, in some embodiments, the fractionation system 30 may perform fractionation of the feedstocks 14 before introduction into the feed system 16, such that any one or combination of polymerization components may be controllably fed into the reactor system 20. For example, the fractionation system 30 may separate monomer components from diluent components to allow monomer and diluent components to be fed separately into the reactor system 20.

The polymer fluff 28 may be further processed within the effluent treatment system 24 and/or in an extrusion/loadout system 36. Although not illustrated, polymer granules and/or active residual catalyst in the effluent treatment system 24 may be returned to the reactor system 20 for further polymerization, such as in a different type of reactor or under different reaction conditions.

In the extrusion/loadout system 36, the polymer fluff 28 is typically extruded to produce polymer pellets 38 with the desired mechanical, physical, and melt characteristics. According to certain embodiments, extruder feed, including additives, such as UV inhibitors and peroxides, may be added to the polymer fluff 28 to impart desired characteristics to the extruded polymer pellets 38. An extruder/pelletizer within the extrusion/loadout system 36 receives the extruder feed, containing the polymer fluff 28 and whatever additives have been added. The extruder/pelletizer heats and melts the extruder feed, which then may be extruded (e.g., via a twin screw extruder) through a pelletizer die of the extrusion/loadout system 36 under pressure to form polyolefin pellets 38. The pellets 38 may be cooled in a water system disposed at or near the discharge of the extruder/pelletizer.

In general, the polyolefin pellets 38 may then be transported to a product load-out area where the pellets may be stored, blended with other pellets, and/or loaded into railcars, trucks, bags, and so forth, for distribution to customers 40. In the case of polyethylene, the polyolefin pellets 38 may include low density polyethylene (LDPE), linear low density polyethylene (LLDPE), medium density polyethylene (MDPE), high density polyethylene (HDPE), and enhanced polyethylene. The various types and grades of polyethylene pellets 38 may be marketed, for example, under the brand names Marlex® polyethylene or MarFlex® polyethylene of Chevron-Phillips Chemical Company, LP, of The Woodlands, Tex., USA.

The polymerization and effluent treatment portions of the polyolefin manufacturing process 10 may be called the "wet end" 42 or "reaction side" of the process 10, while the extrusion/loadout portion of the polyolefin process 10 may be called the "dry end" 44 or "finishing side" of the polyolefin process 10.

The produced polyolefin (e.g., polyethylene) pellets 38 may be used in the manufacture of a variety of products, components, household items and other items, including adhesives (e.g., hot-melt adhesive applications), electrical wire and cable, agricultural films, shrink film, stretch film, food packaging films, flexible food packaging, milk containers, frozen-food packaging, trash and can liners, grocery bags, heavy-duty sacks, plastic bottles, safety equipment, coatings, toys and an array of containers and plastic products. Ultimately, the products and components formed from the polyolefin pellets 38 may be further processed and assembled for distribution and sale to the consumer. For example, a polyethylene milk bottle may be filled with milk for distribution to the consumer, or the fuel tank may be assembled into an automobile for distribution and sale to the consumer.

To form end-products or components from the polyolefin pellets 38, the polyolefin pellets 38 are generally subjected to further processing, such as blow molding, injection molding, rotational molding, blown film, cast film, extrusion (e.g., sheet extrusion, pipe and corrugated extrusion, coating/lamination extrusion, etc.), and so on. Blow molding is a process used for producing hollow plastic parts. The process typically employs blow molding equipment, such as reciprocating screw machines, accumulator head machines, and so on. The blow molding process may be tailored to meet the customer's needs, and to manufacture products ranging from the plastic milk bottles to the automotive fuel tanks mentioned above. Similarly, in injection molding, products and components may be molded for a wide range of applications, including containers, food and chemical packaging, toys, automotive, crates, caps and closures, to name a few.

Extrusion processes may also be used. Polyethylene pipe, for example, may be extruded from polyethylene pellet resins and used in an assortment of applications due to its chemical resistance, relative ease of installation, durability and cost advantages, and the like. Indeed, plastic polyethylene piping has achieved significant use for water mains, gas distribution, storm and sanitary sewers, interior plumbing, electrical conduits, power, and communications ducts, chilled water piping, well casing, to name a few applications. In particular, high-density polyethylene (HDPE), which generally constitutes the largest volume of the polyolefin group of plastics used for pipe, is tough, abrasion-resistant and flexible (even at subfreezing temperatures). Furthermore, HDPE pipe may be used in small diameter tubing and in pipe up to more than 8 feet in diameter. In general, polyethylene pellets (resins) may be supplied for the pressure piping markets, such as in natural gas distribution, and for the non-pressure piping markets, such as for conduit and corrugated piping.

Rotational molding is a high-temperature, low-pressure process used to form hollow parts through the application of heat to biaxially-rotated molds. Polyethylene pellet resins generally applicable in this process are those resins that flow together in the absence of pressure when melted to form a bubble-free part. Polyolefin pellets 38, such as certain Marlex® HDPE and MDPE resins, offer such flow characteristics, as well as a wide processing window. Furthermore, these polyethylene resins suitable for rotational molding may exhibit desirable low-temperature impact strength, good load-bearing properties, and good ultraviolet (UV) stability. Accordingly, applications for rotationally-molded Marlex® resins include agricultural tanks, industrial chemical tanks, potable water storage tanks, industrial waste containers, recreational equipment, marine products, plus many more.

Sheet extrusion is a technique for making flat plastic sheets from a variety of polyolefin pellet resins. The relatively thin gauge sheets are generally thermoformed into packaging applications such as drink cups, deli containers, produce trays, baby wipe containers and margarine tubs. Other markets for sheet extrusion of polyolefin include those that utilize relatively thicker sheets for industrial and recreational applications, such as truck bed liners, pallets, automotive dunnage, playground equipment, and boats. A third use for extruded sheet, for example, is in geomembranes, where flat-sheet polyethylene material is welded into large containment systems for mining applications and municipal waste disposal.

The blown film process is a relatively diverse conversion system used for polyethylene. The American Society for Testing and Materials (ASTM) defines films as less than 0.254 millimeter (10 mils) in thickness. However, the blown film process can produce materials as thick as 0.5 millimeter (20 mils), and higher. Furthermore, blow molding in conjunction with monolayer and/or multilayer coextrusion technologies provide the groundwork for several applications. Advantageous properties of the blow molding products may include clarity, strength, tearability, optical properties, and toughness, to name a few. Applications may include food and retail packaging, industrial packaging, and non-packaging applications, such as agricultural films, hygiene film, and so forth.

The cast film process may differ from the blown film process through the fast quench and virtual unidirectional orientation capabilities. These characteristics allow a cast film line, for example, to operate at higher production rates while producing beneficial optics. Applications in food and retail packaging take advantage of these strengths. Finally, the polyolefin pellets 38 may also be supplied for the extrusion coating and lamination industry.

Figure 2:
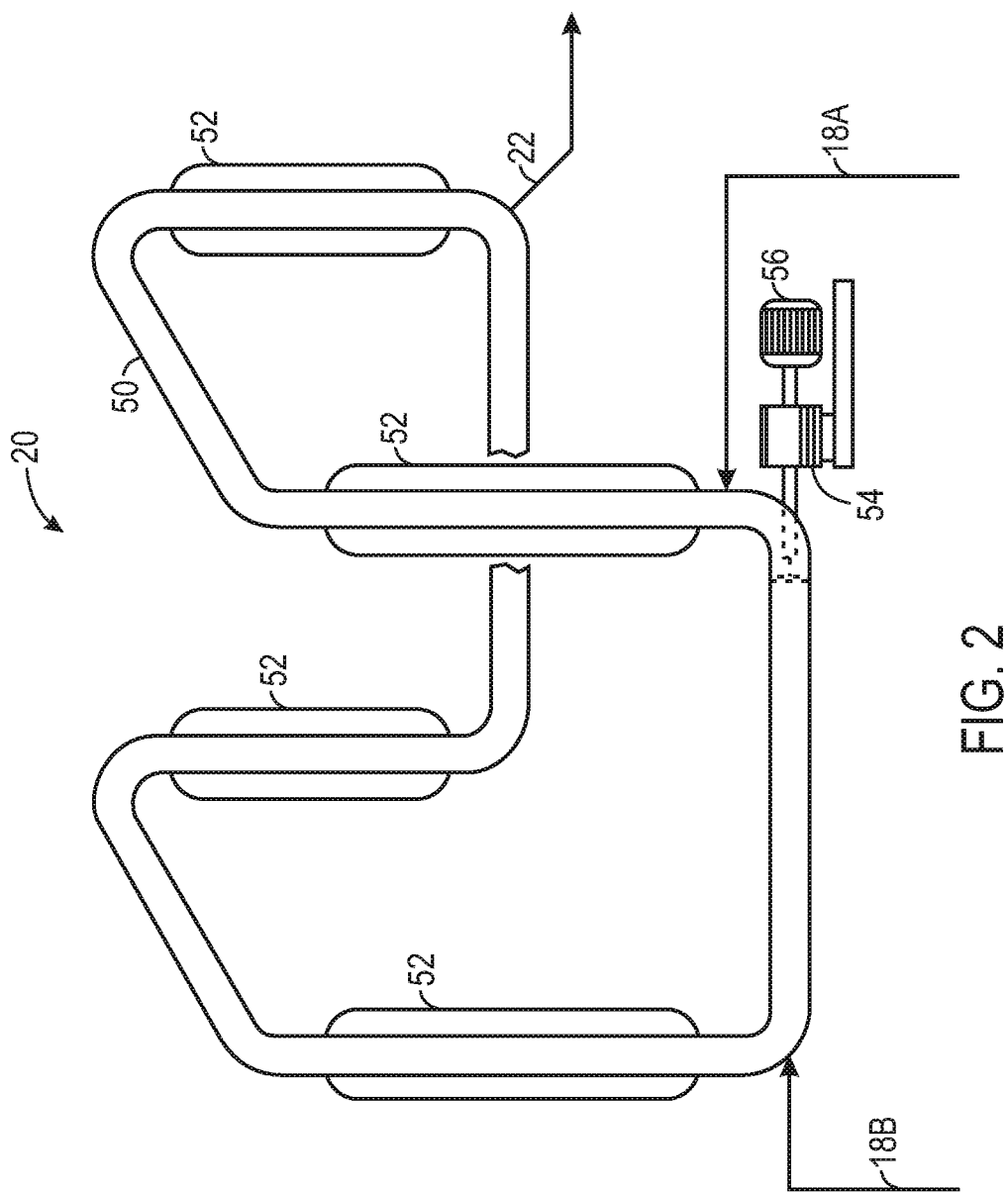
FIG. 2 is a schematic flow diagram of the reactor system of FIG. 1 in accordance with present embodiments.

FIG. 2 depicts an embodiment of the reactor system 20 shown in FIG. 1. As discussed above with respect to FIG. 1, the reactor system 20 may include one or more polymerization reactors of the same or different types. Furthermore, in multiple reactor systems, the reactors may be arranged in series or in parallel. To facilitate explanation, the following examples are limited in scope to specific reactor types believed to be familiar to those skilled in the art and to single reactors or simple combinations. To one of ordinary skill in the art using this disclosure, however, the present techniques are simply and easily applicable to more complex reactor arrangements, such as those involving additional reactors, different reactor types, and/or alternative ordering of the reactors or reactor types. Such arrangements are considered to be well within the scope of the present techniques.

The reactor system 20 includes a liquid phase reactor, such as a loop slurry reactor 50, generally composed of segments of pipe connected by smooth bends or elbows. For simplicity, FIG. 2 depicts a loop slurry reactor 50. However, in other embodiments, the present techniques may be similarly applicable to other types of liquid phase reactors. For example, the reactor system 20 may include other types of liquid phase reactors, such as autoclaves, boiling liquid-pool reactors, or vertical and/or horizontal loop slurry reactors, among others.

As shown, the loop slurry reactor 50 includes four vertical pipe legs formed integrally with horizontal pipe legs (or curved connecting members). According to certain embodiments, the pipe legs may be approximately 24 inches in diameter and approximately 200 feet in length, connected by pipe elbows at the top and bottom of the legs. However, in other embodiments, the diameter, length, and number and/or types of legs may vary. For example, in other embodiments, the loop slurry reactor 50 may include as many as eight to sixteen vertical pipe legs. Further, in other embodiments, more than sixteen vertical pipe legs may be included. In another example, the horizontal members may be eliminated while the vertical legs are connected through curved connecting members. Further, in another example, the pipe legs may be arranged horizontally without vertical pipe legs. In the illustrated embodiment, each leg includes a reactor jacket 52 that may remove heat from the exothermic polymerization via circulation of a cooling medium, such as treated water, through the reactor jacket 52.

In general, the loop slurry reactor 50 may be used to carry out polyolefin polymerization under slurry conditions in which insoluble particles of polyolefin are formed in a fluid medium and are suspended as slurry within the loop slurry reactor 50. A motive device, such as pump 54, circulates the fluid slurry in the reactor 50. According to certain embodiments, the pump 54 may be an in-line axial flow pump with a pump impeller disposed within the interior of the loop slurry reactor 50 to create a turbulent mixing zone within the fluid medium. The impeller also may assist in propelling the fluid medium through the closed loop of the reactor at sufficient speed to keep solid particulates, such as the catalyst and the polyolefin product, suspended within the fluid medium. The impeller may be driven by a motor 56 or other motive force.

The fluid medium, which may be supplied to the reactor 50 by the feed streams 18, may include olefin monomers and comonomers, diluent, co-catalysts (e.g., alkyls, triethylboron, methyl aluminoxane, etc.), molecular weight control agents (e.g., hydrogen), and any other desired co-reactants or additives. For example, feed stream 18A may supply the olefin monomers, olefin comonomers, and diluent components to the reactor 50 via inlets and conduits. Feed stream 18B may supply the catalyst along with a diluent carrier to the reactor 50 via inlets and conduits. For example, the catalyst may include particles suspended in the diluent carrier. The feed stream conduits may be connected to the reactor 50 by flanges, welds, or other suitable types of attachments.

The reaction conditions, such as temperature, pressure, and reactant concentrations, are regulated to facilitate the desired properties and production rate of the polyolefin in the reactor, to control stability of the reactor, and the like. Temperature is typically maintained below the level at which the polymer product would go into solution, swell, soften, or become sticky. As indicated, due to the exothermic nature of the polymerization reaction, a cooling fluid may be circulated through jackets 52 around portions of the loop slurry reactor 50 to remove excess heat, thereby maintaining the temperature within the desired range, generally between 150-250° F. (65-121° C.). Pressure also may be regulated within a desired pressure range, such as 7-55 bar (100-800 psig), with a range of 31-48 bar (450-700 psig) being typical.

As the polymerization reaction proceeds within the reactor 50, the monomer (e.g., ethylene) and comonomers (e.g., 1-hexene) polymerize to form polyolefin (e.g., polyethylene) polymers that are substantially insoluble in the fluid medium at the reaction temperature, thereby forming a slurry of solid particulates within the medium. These solid polyolefin particulates may be removed from the reactor 50 via one or more settling legs, continuous take-offs, or other suitable withdrawal systems, to produce the effluent 22. The effluent 22 may then be processed, for example, within the effluent treatment system 24 (FIG. 1) and the extrusion/loadout system 36 (FIG. 1), to extract and purify the polyolefin particles formed within the reactor 50.

Figure 3:
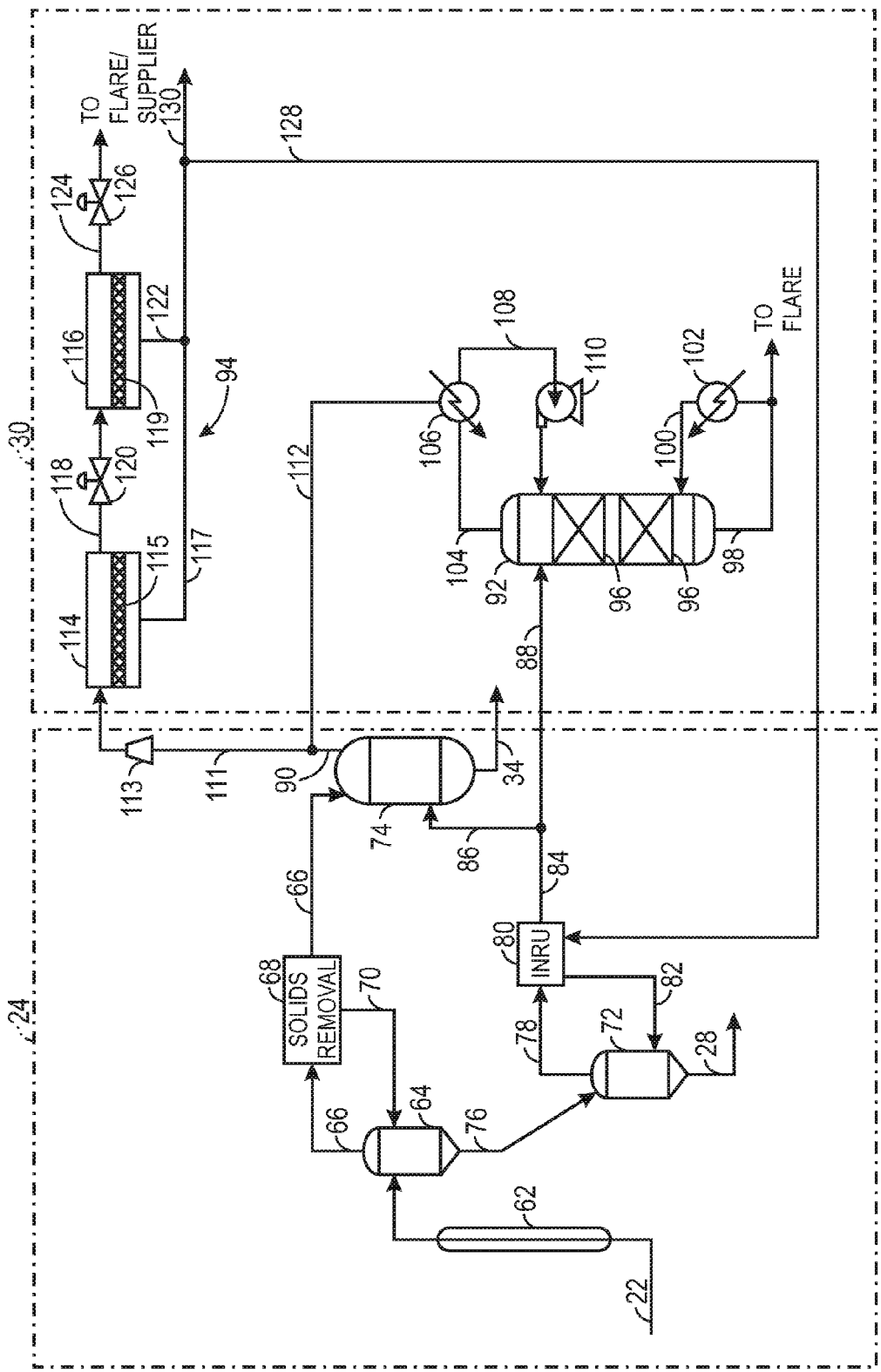
FIG. 3 is a schematic flow diagram of the effluent treatment system and the fractionation system of FIG. 1 in accordance with present embodiments.

FIG. 3 depicts an embodiment of the effluent treatment system 24 and the fractionation system 30 shown in FIG. 1. The effluent 22 from the reactor system 20 (FIG. 2) may be directed to the effluent treatment system 24 where the effluent 22 may flow through an in-line flash heater 62 and into a separation vessel 64. The in-line flash heater 62 may be a surrounding conduit that uses a heating medium, such as steam or steam condensate, to provide indirect heating to the effluent 22 prior to introduction of the effluent 22 into the separation vessel 64. According to certain embodiments, the in-line flash heater 62 may vaporize at least a portion of the diluent within the effluent 22. Moreover, in certain embodiments, the in-line flash heater 62 may be designed to vaporize (i.e. "flash") essentially all of the liquid diluent so that the effluent 22 entering the separation vessel 64 includes solids and vapors, without much liquid. Further, although not shown, water or other catalysts poisons may be injected into the effluent 22 upstream of the separation vessel 64 to deactivate residual catalyst included in the effluent 22. The injected catalyst poisons may be later removed in the recycle fractionation process. For example, the catalyst poisons may be removed within the fractionation system 30.

The separation vessel 64 may include a settling drum, a high efficiency cyclone, a flash gas separator, or combinations thereof, among others. In the separation vessel 64, most of the non-solid components, such as diluent, unreacted monomer, unreacted comonomer, lights, and heavies, rise toward a top portion of the separation vessel 64 and exit the separation vessel 64 in a flash gas stream 66. As noted above, light components or "lights" may be defined as components with lower boiling points than the diluent employed while heavy components or "heavies" may be defined as those components having higher boiling points than the diluent. For example, in embodiments employing isobutane as the diluent, lights may include components such as ethane, propane, or nitrogen, among others, while heavies may include components such as hexane and oligomers, among others.

According to certain embodiments, the flash gas stream 66 may include primarily diluent. For example, in polyolefin production, the flash gas stream 66 may include primarily isobutane. The flash gas stream 66 also may include most of the unreacted monomer (e.g., ethylene) and other light components, as well as unreacted comonomer (e.g., 1-hexene, butene, 1-pentene, 1-octene, and 1-decene) and other heavy components (e.g., hexane and oligomers). According to certain embodiments designed to produce polyethylene, the flash gas 66 may include approximately 94 weight percent isobutane, 5 weight percent ethylene, and 1 weight percent of other components. A level or volume of fluff may be maintained in the separation vessel 64 to provide additional residence time for the fluff in the separation vessel 64. The increased residence time may facilitate separation of the non-polymeric material from the polymer fluff particles.

The flash gas stream 66 may be directed to a solids removal system 68 where entrained polymer solids 70 may be removed and returned to the separation vessel 64. The solids removal system 68 may include equipment, such as cyclones, bag filters, guard filters, and the like, for removing the entrained polymer solids 70 from the flash gas 66. Further, in other embodiments, the removed polymer solids 70 may be directed to downstream equipment, such as a purge column 72, discussed further below. The flash gas stream 66 exiting the solids removal system 68 may then be directed to a recycle tank 74. In other embodiments, the flash gas stream 66 may be directed through additional equipment, such as a de-oxygenation bed and/or a condenser, among others, prior to entering the recycle tank 74. Further, in certain embodiments, the solids removal system 68 may be omitted.

Within the recycle tank 74 some or most of the diluent within the flash gas stream 66 may be condensed to produce the non-fractionated product streams 34 that are returned to the reactor system 20 through the feed system 16, as shown in FIG. 1. The non-fractionated product streams 34 exiting the recycle tank 74 are directly recycled to the reactor system 20 without passing through the fractionation system 30. As discussed above with respect to FIG. 1, the non-polymeric material 26 exiting the effluent treatment system 24 may be returned to the reactor system 20 through both the non-fractionated product streams 34 and the fractionated product streams 32. According to certain embodiments, at least approximately 50-99 percent of the non-polymeric material 26 may be recycled, recovered, or fractionated within the manufacturing system 10. In general, most of the material exiting the effluent treatment system 24 may be directly recycled as non-fractionated product streams 34, with a relatively small portion of the material exiting the effluent treatment system 24 being directed as one or more slip streams to the fractionation system 30. The relatively small portion of material entering the fractionation system 30 may allow equipment within the fractionation system 30 to be reduced in size.

Within the separation vessel 64, the solid components, which are mostly polymer fluff, may fall to a bottom portion of the separation vessel 64 where the solid components may be withdrawn as a solids discharge 76 and directed to the purge column 72. The solids discharge 76 also may include a small amount of entrained diluent and/or entrained monomer.

Although not shown, the solids discharge 76 may flow through one or more valve configurations that allow the solids discharge 76 to flow downward to the purge column 72 while reducing the potential for vapor to flow between the purge column 72 and the separation vessel 64. For example, the solids discharge 76 may be directed through equipment, such as one or more rotary or cycling valves, a single Vee-Ball® control valve, fluff surge tanks, or a relatively small fluff chamber, among others, prior to entering the purge column 72. According to certain embodiments, a level of solid components may be maintained in the separation vessel 64, for example, via a level control valve, which may increase the residence time of the solid components in the separation vessel 64, thereby promoting improved separation of the solid and non-solid components. Further, certain configurations may provide for continuous fluff discharge from the separation vessel 64, which may eliminate one or more cycling valves.

Within the purge column 72, purge gas may be employed to remove residual hydrocarbons, such as entrained diluent, heavies, and lights, from the solid components. For example, nitrogen may be fed to the purge column 72 to remove residual hydrocarbons in a residual hydrocarbon stream 78 that may exit the purge column 72 as overhead discharge. Removal of the residual hydrocarbons may yield the polymer fluff 28, which may be removed from the purge column 72 and directed to the extrusion/loadout system 36 for further processing as described above with respect to FIG. 1.

The residual hydrocarbon stream 78, containing the nitrogen purge gas and the extracted residual hydrocarbons, may be sent through a separation unit 80. According to certain embodiments, the separation unit 80 may include a membrane recovery unit, pressure swing adsorption unit, or a refrigeration unit, among others. In the art, the separation unit 80 may be known as a Diluent Recovery Unit (DRU). Further, in some embodiments, such as the manufacturing system 10 (FIG. 1) employing isobutane diluent, the separation unit 80 may be an Isobutane Nitrogen Recovery Unit (INRU).

Within the separation unit 80, the purge gas may be separated from the extracted residual hydrocarbons. Accordingly, the separation unit 80 may produce a purge gas stream 82 and a stream 84 that contains the residual hydrocarbons. The purge gas stream 82 may be directed to the purge column 72 to extract more residual hydrocarbons from the polymer fluff. Further, although not shown, fresh purge gas, such as nitrogen, may be added with the recovered purge gas 82 to make up for purge gas losses within the purge column 72.

The stream 84 may be separated into two streams 86 and 88, each containing diluent, heavies, and lights. According to certain embodiments, the streams 86 and 88 may primarily contain diluent and heavies. However, the streams 86 and 88 also may contain some lights. The stream 86 may be directed to the recycle tank 74. According to certain embodiments, the recycle tank 74 may be designed to function as a vapor-liquid separation drum that flashes, or otherwise separates, the lights from the liquid diluent and heavies. For example, the lights may collect in a top portion of the recycle tank 74 and may exit the recycle tank 74 in a vapor stream 90 that enters the fractionation system 30. The stream 88 also may be directed to the fractionation system 30. Specifically, the stream 88 may be directed to a heavies fractionation column 92 within the fractionation system 30.

As may be appreciated, the effluent treatment system 24 is provided by way of example only, and it not intended to be limiting. For example, the effluent treatment system 24 may employ other equipment and/or configurations. According to certain embodiments, the purge column 72 may be replaced by another reactor, such as a gas phase reactor. In other embodiments, the solids discharge 76 from the separation vessel 64 may be directed through a low-pressure flash chamber prior to entering the purge column 72. Further, the purge column 72 may be combined with equipment, such as an extruder feed tank, located in the extrusion/loadout system 36.

The fractionation system 30 may receive and process the residual hydrocarbons exiting the effluent treatment system 24. For example, the fractionation system 30 may receive the residual hydrocarbons through the vapor stream 90 exiting the recycle tank 74 and through the stream 88 exiting the separation unit 80. As noted above, the residual hydrocarbons may include diluent, lights, such as unreacted monomer (e.g., ethylene), ethane, and inerts, among others, and heavies, such as unreacted comonomer (e.g., 1-hexene), oligomers, hexane, and the like. In general, the fractionation system 30 may be designed to remove heavies and lights from the diluent to impede the build up of heavies and lights within manufacturing system 10 (FIG. 1). The fractionation system 30 may include the heavies fractionation column 92, which may be designed to remove heavies from the diluent, and a membrane system 94, which may be designed to remove lights from the diluent.

To prevent the build up of heavies within the manufacturing system 10 (FIG. 1), a portion or all of the extracted hydrocarbons exiting the separation unit 80 may be directed to the heavies fractionation column 92 through the stream 88. In general, the heavies fractionation column 92 may use distillation to separate the hydrocarbon components based on their different boiling points, for example, by preferentially boiling the more volatile components out of the stream 88. According to certain embodiments, the heavies fractionation column 92 may operate at a pressure of approximately 9-12 bar (125-175 psig) and a temperature of approximately 60-177° C. (140-350° F.). However, in other embodiments, the temperature and pressure ranges may vary.

Within the heavies fractionation column 92, liquid and vapor may typically flow counter-currently, contacting each other through internals 96. The internals 96 may include trays, plates, and packing, among others, and may be used to create stages that provide improved contact between the liquid and vapor flows, thereby, promoting separation. The heavies may generally condense within the column and flow to a bottom portion of the column 92. The heavies may then exit the heavies fractionation column 92 in a bottoms discharge 98, which may be directed to a flare, to an incinerator, or to a tank for disposal.

The bottoms discharge 98 may generally include the least volatile components, for example, components with a boiling point that is less than the boiling point of the diluent. According to certain embodiments employing the diluent isobutane, the heavies may include hexane, hexene, and oligomers, among others. A portion 100 of the bottoms discharge 98 may be directed through a reboiler 102 where a heating medium, such as steam or steam condensate, may be used to vaporize some of the portion 100. The vapor exiting the reboiler 102 may be returned to the heavies fractionation column 92 to facilitate further separation of the components within the heavies fractionation column 92. For example, the portion 100 exiting the reboiler 102 may be directed to a bottom portion of the column where the vapor may flow up the heavies fractionation column 92 in countercurrent flow with the liquid flowing down the heavies fractionation column 92.

As the stream 88 flows down the heavies fractionation column 92, the more volatile components may vaporize and collect within a top portion of the heavies fractionation column 92. The more volatile components may then exit the heavies fractionation column 92 as an overhead discharge stream 104 that may include primarily diluent, such as isobutane, and lights, such as ethylene and ethane, hydrogen, and nitrogen, among others. In general, the heavies fractionation column 92 may separate components based on their boiling points to produce the bottoms discharge 98, which is concentrated with the heavies, and the overhead discharge 104, which is concentrated with the lights and the diluent.

The overhead discharge stream 104 may be directed through a condenser 106 where a portion 108 of the overhead discharge stream 104 may be condensed and used as reflux for the heavies fractionation column 92. In particular, the condensed portion 108 may be returned to an upper section of the heavies fractionation column 92 via a pump 110. In certain embodiments the condenser 106 may include a shell and tube heat exchanger or other type of heat exchanger. Further, an accumulator may be included with the condenser 106 to promote separation of the condensed liquid from the vapor.

The vaporized portion of the overhead discharge stream 104 may exit the condenser 106 as a vapor stream 112 that may be combined with the vapor stream 90 exiting the recycle tank 74 to form a stream 111 that is directed to the membrane system 94. Because most of the heavies are removed within the heavies fractionation column 92 and/or within the recycle tank 74, the vapor streams 90 and 112 may contain primarily diluent and lights. However, some heavies that may have a boiling point slightly higher than the diluent, such a comonomer (e.g., 1-butene), may also be included within the vapor streams 90 and 112. For example, in certain embodiments, the vapor streams 90 and 112 may contain approximately 5-20 percent by weight of 1-butene.

The vapor streams 90 and 112 may be directed to the membrane separation system 94 where the lights may be separated. As shown, the vapor streams 90 and 112 are combined into a single feed stream 111 prior to entering the membrane separation system 94. However, in other embodiments, the vapor streams 90 and 112 may enter the membrane separation system 94 as separate streams. Further, in certain embodiments, the feed stream 111 may be directed through a compressor 113 prior to entering the membrane separation system 94. However, in other embodiments, the compressor 113 may be omitted or may be part of the membrane separation system 94.

The membrane separation system 94 may include one or more membrane modules 114 and 116 designed to separate lights and heavies. The membrane modules 114 and 116 may include hydrocarbon absorption membranes 115 and 119 designed to separate hydrocarbons and other components based on solubility, molecular size, or both. In certain embodiments where isobutane is employed as the diluent, the hydrocarbon absorption membranes may be designed to separate lights, such as ethylene, ethane, and nitrogen, among others, from the diluent isobutane. The membrane modules 114 and 116 may include any suitable type of gas separation membrane modules, such as spiral wound or hollow-fiber membrane modules, among others. According to certain embodiments, the membrane modules 114 and 116 may include VaporSep® membrane modules commercially available from Membrane Technology and Research, Inc. of Menlo Park, Calif.

Each membrane module 114 and 116 may include gas separation membranes 115 and 119 with one or more layers designed to promote separation of the diluent and lights. For example, the membranes 115 and 119 may include a nonwoven fabric layer designed to serve as a substrate, a solvent resistant microporous support layer designed to provide mechanical support, and a nonporous selective layer that performs the separation. In certain embodiments, the microporous support layer and the nonporous selective layer may be cross-linked to one another.

As shown in FIG. 3, the membranes 115 and 119 may be designed to allow larger hydrocarbon molecules to permeate through the membranes 115 and 119 while retaining smaller hydrocarbon molecules and other smaller molecules on the other side of the membrane 115 and 119. For example, where the membranes 115 and 119 are designed to separate molecules by solubility, the membranes 115 and 119 may include a selective layer of a rubbery polymer, such as silicone rubber, that allows larger hydrocarbon molecules to permeate the membranes 115 and 119 based on their higher solubility in the membrane polymer. In another example, where the membranes 115 and 119 are designed to separate molecules by size, the membranes 115 and 119 may include a selective layer that separates the diluent from the lights based on different diffusion rates. According to certain embodiments where the diluent is isobutane, the membranes 115 and 119 may be designed to allow hydrocarbons having four or more carbons to permeate the membranes 115 and 119 while retaining hydrocarbons with three or fewer carbon atoms as well as other smaller components.

The feed stream 111, which, as noted above, contains primarily diluent and lights, may enter the membrane separation system 94 and flow through the first membrane module 114. Within the first membrane module 114, the diluent, which has relatively larger hydrocarbon molecules than the lights, may permeate the membrane 115 and exit the first membrane module 114 in a diluent enriched steam 117. The diluent enriched stream 117 contains primarily diluent; however, small amounts of entrained heavies and lights may also be present. According to certain embodiments, the diluent enriched stream 117 may contain at least 50, 60, 70, 80, or 90 percent by weight of diluent. The lights, which have relatively smaller hydrocarbon molecules, may be retained by the membrane 115 and may exit the membrane module 114 in a lights enriched stream 118. The lights enriched stream 118 may contain primarily lights; however, small amounts of entrained diluent and heavies may also be present. According to certain embodiments, the lights enriched stream 118 may contain at least 40, 50, 60, 70, 80, or 90 percent by weight of lights. In certain embodiments, the lights enriched stream 118 may flow through one or more valves 120 which may be adjusted to regulate the driving force across the membrane module 114.

The lights enriched stream 118 may then enter the second membrane module 116 where some or all of the entrained diluent may be removed. Specifically, the diluent may permeate the membrane 119 and may exit the membrane module 116 in a diluent enriched stream 122, while the lights may be retained by the membrane 119 and may exit the membrane module 116 in a lights enriched stream 124. In certain embodiments, the lights enriched stream 124 may flow through one or more valves 126 which may be adjusted to regulate the driving force across the membrane module 116.

The lights enriched stream 124 may contain primarily lights and may be directed to a flare to remove the lights from the manufacturing system 10 (FIG. 1). According to certain embodiments, the lights enriched stream 124 may contain at least 50, 60, 70, 80, or 90 percent by weight of lights. In embodiments where the diluent is isobutane, the lights enriched stream 124 may include components such as ethane, inerts, such as nitrogen, and unreacted monomer, such as ethylene. In certain embodiments, some or all of the lights enriched stream 124 may be directed to additional processing systems where some of the lights, such as the unreacted monomer, may be recovered and provided to a supplier. For example, where the monomer is ethylene, the lights enriched steam 124 may be directed to an ethylene unit in a polyethylene manufacturing process.

The diluent enriched stream 122 may contain primarily diluent and may be combined with the diluent enriched stream 117 exiting the first membrane module 114 to form a single diluent enriched stream 128. According to certain embodiments, the diluent enriched stream 128 may contain at least 30, 40, 50, 60, 70, 80, or 90 percent by weight of diluent. The diluent enriched steam 128 may be directed to the separation unit 80 where the diluent may be further extracted. However, in other embodiments, the diluent enriched streams 122 and 117 may be provided to the separation unit 80 as separate streams. Further, in certain embodiments, a portion 130 of the diluent enriched stream 128 may be withdrawn and used in catalyst preparations and/or in reactor flushes.

The membrane separation system 94 may include any number of membrane modules, such as the membrane modules 114 and 116, as well as other equipment. For example, at least one, two, or three membrane modules may be included within the membrane system 94. In certain embodiments, the membrane system 94 may be provided as a skid that includes the membrane modules 114 and 116, which may be surrounded by pressure vessels, and/or may include additional equipment, such as compressors, pumps, heat exchangers, and vapor-liquid separators, among others. Further, the membrane separation system 94 may include instrumentation and control systems. For example, the membrane separation system 94 may be compatible with a Distributed Control System (DCS) or with a Programmable Logic Controller (PLC) based control system. Moreover, in other embodiments, the membrane separation system 94 may be part of other equipment within the fractionation system 30. For example, the membrane separation system 94 may be integrated with the heavies fractionation column 92 as a top portion of the heavies fractionation column 92.

Figure 4:
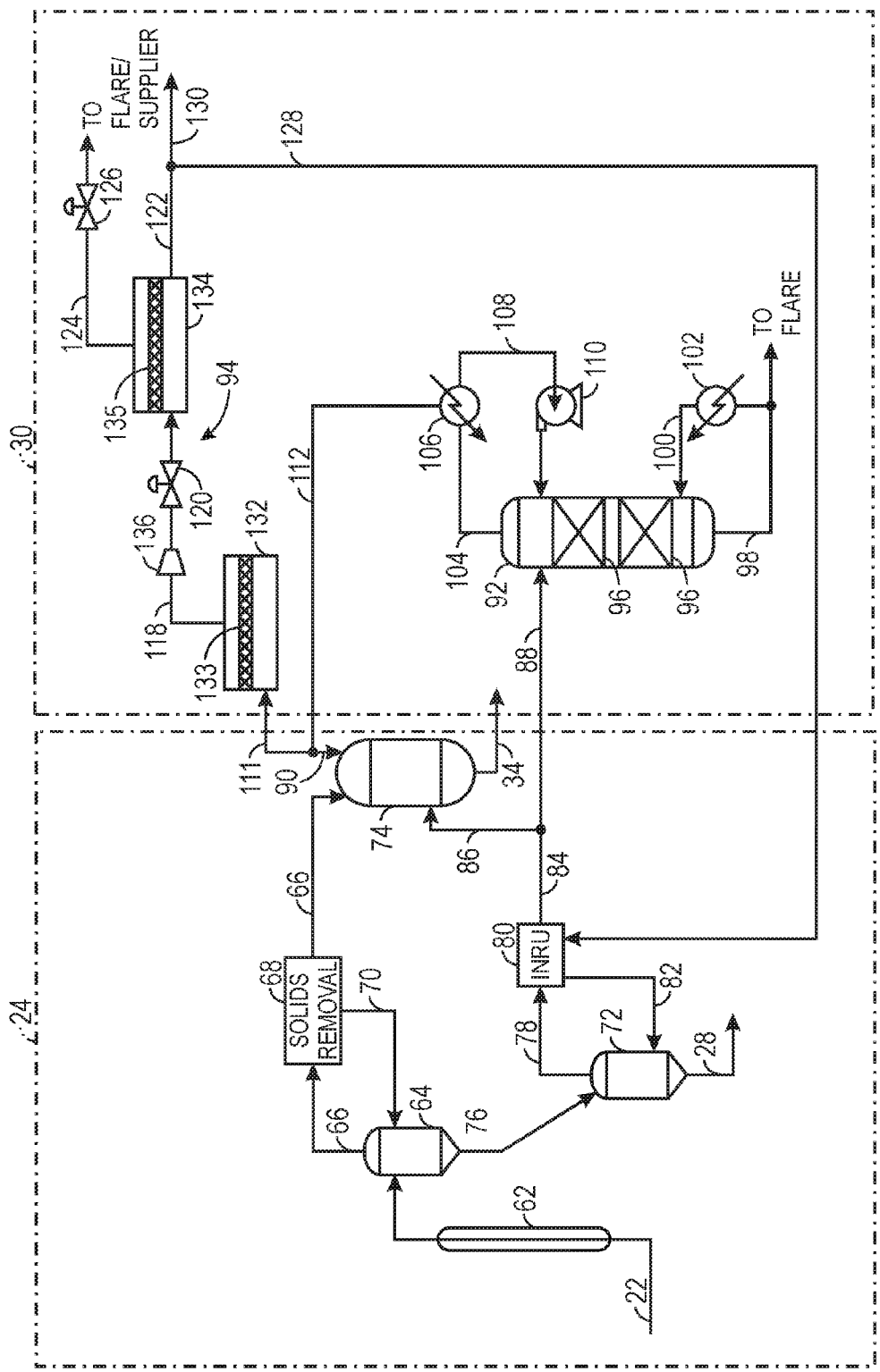
FIG. 4 is a schematic flow diagram of another embodiment of the fractionation system of FIG. 1 in accordance with present embodiments.

FIG. 4 depicts another embodiment of the membrane separation system 94 that may be employed within the fractionation system 30. As shown in FIG. 4, the membrane separation system 94 includes membrane modules 132 and 134 with membranes 133 and 135 that are designed to retain diluent rather than allowing the diluent to permeate through the membranes 115 and 119 as shown in FIG. 3. Similar to the membranes 115 and 119 described above with respect to FIG. 3, the membranes 133 and 135 may separate the lights and the diluent based on molecular size, solubility, or both. For example, according to certain embodiments, the membranes 133 and 135 may include glassy polymers that allow smaller hydrocarbon molecules to permeate the membranes 133 and 135 while impeding the passage of larger hydrocarbon molecules, such as the diluent.

As described above with respect to FIG. 3, the heavies fractionation column 92 and the recycle tank 74 may remove heavies from the streams 88 and 84. The membrane separation system 94 may then receive a combined feed stream 111 that includes the vapor steams 90 and 112 exiting the recycle tank 74 and the heavies fractionation column 92, respectively. However, in other embodiments, the vapor streams 90 and 112 may enter the membrane separation system 94 as separate streams. Within the membrane separation system 94, the feed stream 111 may flow through the first membrane module 132. The lights may permeate the membrane 133 and may exit the first membrane module 132 in the lights enriched stream 118. The diluent, on the other hand, may be retained within the first membrane module 132. Further, in certain embodiments, the diluent, as well as entrained heavies, may be directed back to the recycle tank 74 as counterflow within the vapor stream 90. In certain embodiments, the design of the membrane module 132, which allows lights to permeate the membrane 133 while impeding the passage of diluent and heavies, may inhibit the flow of entrained heavies into the membrane separation system 94. Further, in certain embodiments, the driving force created by inhibiting the passage of diluent through the membrane 133 may reduce the need for a compressor in the vapor stream 90.

The lights enriched steam 118 exiting the first membrane module 132 may be directed through a compressor 136 that may be designed to compress the lights enriched stream 118 prior to entry into the second membrane module 134. Within the second membrane module 134, the lights may permeate the membrane 135 and exit the membrane module 134 as the lights enriched stream 124. The lights enriched stream 124 may then be directed to a flare or to further processing as described above with respect to FIG. 3. The diluent retained by the membrane 135 may exit the second membrane module 134 as the diluent enriched stream 122. According to certain embodiments, the diluent enriched stream 122 may be separated into the portion 130, which may used for catalyst flushes and the like, and the diluent enriched stream 128 that may directed to the separation unit 80.

As discussed above with respect to FIG. 3, the membrane separation system 94 may include additional equipment, such as the valves 120 and 126 that may be adjusted to regulate the driving forces across the membrane modules 132 and 134. Further, in certain embodiments, the membrane separation system 94 may be provided as a skid or may be integrated into other equipment within the fractionation system 30. Moreover, combinations of the membrane modules described herein may be employed within membrane separation systems. For example, in certain embodiments, a membrane separation system may use one or more membrane modules designed to retain diluent, as described with respect to FIG. 4, in combination with one or more membrane modules designed to retain lights, as described with respect to FIG. 3.

While the present disclosure may be susceptible to various modifications and alternative forms, specific embodiments have been shown by way of example in the drawings and tables and have been described in detail herein. However, it should be understood that the embodiments are not intended to be limited to the particular forms disclosed. Rather, the disclosure is to cover all modifications, equivalents, and alternatives falling within the spirit and scope of the disclosure as defined by the following appended claims. Further, although individual embodiments are discussed herein, the disclosure is intended to cover all combinations of these embodiments.

What is claimed is:

1. A method for recovering diluent from polymerization reactor effluent, the method comprising:
    separating effluent from a polymerization reactor into extracted polyolefin solids, a first stream including primarily diluent and heavy components, and a second stream including primarily the diluent and light components;
    fractionating the first stream in a heavies fractionation column to produce a first discharge stream including primarily the heavy components and a second discharge stream including primarily the diluent; and
    separating the second stream in a membrane separation system to produce a diluent enriched stream including primarily the diluent and a lights enriched stream including primarily the light components, wherein the membrane separation system is an integral top portion of the heavies fractionation column.

2. The method of claim 1, comprising polymerizing olefin monomer in a loop slurry polymerization reactor in the presence of catalyst suspended in the diluent to form the polyolefin solids and discharging the effluent from the polymerization reactor.

3. The method of claim 1, comprising separating the second stream in the membrane separation system using at least one membrane having a nonwoven fabric layer, a solvent resistant microporous support layer, and a nonporous selective layer.

4. The method of claim 3, wherein the solvent resistant microporous support layer and the nonporous selective layer are cross-linked to one another.

5. The method of claim 1, wherein separating the second stream in the membrane separation system comprises directing the second stream through one or more separation membranes configured to permeate the light components through the one or more separation membranes.

6. The method of claim 1, comprising separating the second stream in the membrane separation system using a first membrane module and a second membrane module.

7. The method of claim 6, wherein separating the second stream in the membrane system using the first membrane module and the second membrane module comprises:
    separating the second stream into a first lights enriched stream and a first isobutane enriched stream in the first membrane module, wherein the first lights enriched stream includes primarily light components , and wherein the first isobutane enriched stream includes primarily isobutane; and
    separating the first lights enriched stream into a second lights enriched stream and a second isobutane enriched stream in the second membrane module, wherein the second lights enriched stream includes primarily light components, and wherein the second isobutane enriched stream includes primarily isobutane.

8. The method of claim 7, wherein separating the second stream into the first lights enriched stream and the first isobutane enriched stream comprises directing the second stream through a membrane of the first membrane module, the membrane being configured to permeate hydrocarbons with four or more carbon atoms and to substantially block hydrocarbons with three or fewer carbon atoms.

9. The method of claim 7, wherein separating the first lights enriched stream into the second lights enriched stream and the second isobutane enriched stream comprises directing the first lights enriched stream through a membrane of the second membrane module, the membrane being configured to permeate hydrocarbons with four or more carbon atoms and to substantially block hydrocarbons with three or fewer carbon atoms.

10. The method of claim 7, comprising combining the first isobutane enriched stream from the first membrane module and the second isobutane enriched stream from the second membrane module in an isobutane enriched flow path.

11. The method of claim 7, comprising conveying the first lights enriched stream from the first membrane module to the second membrane module via a first lights enriched flow path.

12. The method of claim 7, comprising:
conveying the second lights enriched stream to a flare or a processing system; and
conveying the second isobutane enriched stream directly to a separation unit.

13. The method of claim 1, comprising combining the second discharge stream from the heavies fractionation column with the second stream upstream of the membrane separation system.

14. The method of claim 1, comprising directing the lights enriched stream to a flare or to a monomer recovery unit.

15. A method for producing polyolefin solids, comprising:
polymerizing an olefin monomer in a polymerization reactor to produce a slurry having polyolefin solids, isobutane, heavy components, and light components;
discharging the slurry from the polymerization reactor as an effluent;
producing a first stream, a second stream, and polyolefin solids from the effluent in an effluent treatment system;
fractionating the first stream in a heavies fractionation column to produce a first discharge stream including primarily the heavy components and a second discharge stream including primarily the light components and the isobutane;
separating the second stream in a membrane separation system to produce an isobutane enriched stream including primarily the isobutane and a lights enriched stream including primarily the light components;
recycling at least a portion of the isobutane enriched stream directly to a separation unit of the effluent treatment system; and
processing the polyolefin solids to produce polyolefin fluff.

16. The method of claim 15, wherein producing the first stream comprises separating a purge gas from a residual hydrocarbon stream to produce a purge gas recycle stream and the first stream in the separation unit.

17. The method of claim 15, wherein at least a portion of the second stream comprises the second discharge stream from the heavies fractionation column.

18. The method of claim 15, comprising separating the second stream in the membrane separation system through at least one membrane comprising a nonwoven fabric layer, a solvent resistant microporous support layer, and a nonporous selective layer, wherein the solvent resistant microporous support layer and the nonporous selective layer are cross-linked to one another.

19. The method of claim 15, wherein the membrane separation system is an integral top portion of the heavies fractionation column.

20. A method for producing polyolefin solids, comprising:
producing a first stream, a second stream, and polyolefin solids from effluent discharged from a polymerization reactor in an effluent treatment system;
fractionating the first stream in a heavies fractionation column to produce a first discharge stream including primarily heavy components and a second discharge stream including primarily light components and isobutane;
separating the second stream in a membrane separation system to produce an isobutane enriched stream including primarily the isobutane and a lights enriched stream including primarily the light components;
recycling at least a portion of the isobutane enriched stream directly to a separation unit of the effluent treatment system; and
processing the polyolefin solids to produce polyolefin fluff.

* * * * *